US00PP37181P2

(12) United States Plant Patent
Guo

(10) Patent No.: US PP37,181 P2
(45) Date of Patent: Dec. 30, 2025

(54) ***KALANCHOE* PLANT NAMED 'KLEKB24053'**

(50) Latin Name: *Kalanchoe blossfeldiana*
Varietal Denomination: KLEKB24053

(71) Applicant: KLEMM + SOHN GMBH & CO. KG, Stuttgart (DE)

(72) Inventor: Huijuan Guo, Kornwestheim (DE)

(73) Assignee: Klemm + Sohn Gmbh & Co. KG, Stuttgart (DE)

( * ) Notice: Subject to any disclaimer, the term of this patent is extended or adjusted under 35 U.S.C. 154(b) by 0 days.

(21) Appl. No.: 19/286,026

(22) Filed: Jul. 30, 2025

(51) Int. Cl.
*A01H 5/02* (2018.01)

(52) U.S. Cl.
USPC ..... Plt./340

(58) Field of Classification Search
USPC ..... Plt./263.1, 335, 340
See application file for complete search history.

(56) References Cited

U.S. PATENT DOCUMENTS

PP33,683 P2 * 11/2021 Vlielander ..... Plt./341

* cited by examiner

*Primary Examiner* — Karen M Redden
(74) *Attorney, Agent, or Firm* — Weatherly IP Solutions, LLC; Karen P. Bechtold; James Weatherly

(57) ABSTRACT

A new *Kalanchoe* plant particularly distinguished by yellow Flowers with a large orange center; and a vigorous, upright and free flowering plant habit with numerous cymes positioned above the foliar plane; is disclosed.

1 Drawing Sheet

Genus and species: *Kalanchoe blossfeldiana.*
Variety denomination: 'KLEKB24053'.

BACKGROUND OF THE NEW PLANT

The present invention comprises a new and distinct variety of *Kalanchoe*, botanically known as *Kalanchoe blossfeldiana* and hereinafter referred to by the variety name 'KLEKB24053'. 'KLEKB24053' originated from a controlled cross between proprietary female *Kalanchoe* variety 'KA-2017-FV13018' (unpatented) and proprietary male *Kalanchoe* variety '1106-4' (unpatented) in Kenya in December 2019.

A plant line was selected in June 2020 and subsequently named 'KLEKB24053'. In July 2020, 'KLEKB24053' was first vegetatively propagated by vegetative terminal cuttings in Stuttgart, Germany. 'KLEKB24053' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Yellow flowers with a large orange center; and
2. A vigorous, upright and free flowering plant habit with numerous cymes positioned above the foliar plane.

DESCRIPTION OF THE PHOTOGRAPH

This new *Kalanchoe* plant is illustrated by the accompanying photograph which shows an overall view of the plant. The photograph is of an approximately 12-week-old plant grown in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLEKB24053'. The data which define these characteristics were collected from asexual reproductions carried out in Stuttgart, Germany. Data was collected in June 2025 on 14-week-old plants grown Stuttgart, Germany grown in a greenhouse. Color references are to The R.H.S. Colour Chart of The Royal Horticultural Society of London (R.H.S.), 5$^{th}$ edition (2007).

Classification:
- *Family.*—Crassulaceae.
- *Botanical.—Kalanchoe blossfeldiana.*
- *Designation.*—'KLEKB24053'.

Parentage:
- *Female parent.*—'KA-2017-FV13018' (unpatented).
- *Male parent.*—'1106-4' (unpatented).

Propagation:
- *Type.*—By vegetative terminal cuttings.
- *Time to initiate roots, summer.*—About 11 days at temperatures about 20° C.
- *Time to initiate roots, winter.*—About 14 days at temperatures about 20° C.
- *Time to produce a rooted young plant, summer.*—About three weeks at temperatures about 20° C.
- *Time to produce a rooted young plant, winter.*—About four weeks at temperatures about 21° C.
- *Root description.*—Moderately freely branching, fine, fibrous.
- *Root color.*—RHS N155C.

Plant description:

*Plant and growth habit*.—Vigorous and upright plant habit, freely flowering habit with numerous cymes positioned above the foliar plane, rounded crown, can culture in the pots with diameter 6.0 to 12.0 cm.

*Plant height at flowering*.—22.5 cm.

*Plant diameter at flowering*.—25.0 cm.

*Branching habit*.—Freely branching habit with about 8 lateral branches developing per plant.

*Lateral branch description*.—Length: About 17.0 cm. Diameter: About 8.0 cm to 10.0 cm. Internode length: About 3.0 cm to 6.0 cm. Aspect: Mostly upright. Strength: Strong. Texture: Smooth, glabrous. Color: Developing: RHS 143C. Developed: RHS 143B.

Leaf description:

*Arrangement*.—Opposite, single, generally symmetrical.

*Quantity of leaves per lateral branch*.—3 pairs.

*Length*.—About 1.5 cm to 4.5 cm.

*Width*.—About 1.5 cm to 3.5 cm.

*Shape*.—Ovate.

*Apex*.—Obtuse.

*Base*.—Obtuse.

*Margin*.—Broadly crenate.

*Texture*.—Upper surface: Smooth, glabrous, coriaceous, succulent, glossy. Lower surface: Smooth, glabrous, coriaceous, succulent, glossy.

*Venation pattern*.—Pinnate.

*Color*.—Developing leaves: Upper surface: RHS 137A. Lower surface: RHS 137C. Fully developed leaves Upper surface: RHS N137A. Lower surface: RHS 137B.

Petioles:

*Length*.—0.2 cm.

*Diameter*.—0.3 cm.

*Strength*.—Strong.

*Texture*.—Smooth, glabrous, coriaceous, succulent.

*Color*.—Upper surface: RHS N137C. Lower surface: RHS 137D.

Flower description:

*Flower arrangement and habit*.—Filled flowers arranged in axillary cymes, uniform and freely flowering habit, continuously for 9 weeks.

*Fragrance*.—Absent.

*Natural flowering season*.—Initiate and develop flowers under short day and long night conditions or during November and December in the Northern Hemisphere; buds and flowers can also be induced under artificial short day/long night conditions with about 14 hours darkness.

*Time to flower*.—Medium, plants begin flowering around 15 and a half weeks after potting.

*Post-production longevity*.—Very good post-production longevity, plants maintain good foliage and flower substance, can keep flowering for more than 9 weeks.

Flower diameter.—2.5 cm.

*Flower length* (*height*).—1.6 cm.

*Flower bud*.—Length: 1.8 cm. Diameter: 0.5 cm. Shape: Initially oblong, becoming tubular ovoid with development. Texture: Smooth, glabrous, glossy. Color: Flower tip: RHS N25D. Flower center: RHS N30B.

Petals:

*Arrangement*.—About 4 petals in one layer.

*Length*.—1.2 cm.

*Width*.—1.2 cm.

*Aspect*.—Flat.

*Shape*.—Ovate to round.

*Apex*.—Acute.

*Base*.—Obtuse.

*Margin*.—Entire.

*Texture*.—Upper surface: Smooth, glabrous, glossy. Lower surface: Smooth, glabrous, matte.

*Color*.—When opening: Upper surface: RHS N25D at tip, RHS N30B at bottom. Lower surface: RHS 24C. Fully opened: Upper surface: RHS N25D at tip; RHS N30B at bottom. Lower surface: RHS 24C.

Sepals:

*Appearance*.—Four to five in a single whorl.

*Length*.—1.0 cm.

*Width*.—0.4 cm.

*Shape*.—Oblong, pointed.

*Apex*.—Acute.

*Base*.—Obtuse.

*Margin*.—Entire.

*Aspect*.—Upright.

*Texture*.—Upper surface: Smooth, glabrous, glossy. Lower surface: Smooth, glabrous, glossy.

*Color*.—Upper surface: RHS 143A. Lower surface: RHS 143B.

Peduncles:

*Length*.—0.5 cm to 0.6 cm.

*Diameter*.—0.1 cm.

*Aspect*.—Erect.

*Strength*.—Medium strong.

*Texture*.—Smooth and glabrous.

*Color*.—RHS 138A.

Reproductive organs:

*Androecium*.—Stamen number: Eight per flower. Filament color: RHS 143C. Anther length: 0.1 cm. Anther shape: Elliptic. Anther color: RHS 144D. Amount of pollen: Many. Pollen color: RHS 12B.

*Gynoecium*.—Pistil number: 4 to 5. Pistil length: 1.2 cm. Style length: 0.4 cm. Style color: RHS 144B. Stigma shape: Round and fluffy. Stigma color: RHS 144C. Ovary color: RHS 144A.

Seeds:

*Quantity per flower*.—If developed, up to 100 seeds.

*Length*.—About 0.01 cm.

*Diameter*.—About 0.05 cm.

*Texture*.—Rough.

*Color*.—RHS 166C.

Temperature tolerance: Plants have been observed to tolerate temperatures from 15° C. to 35° C.

Disease and pest/insect resistance: Plants have been observed to have tolerance to Power Mildew (*Erysiphe cichoraceaum*).

COMPARISON WITH PARENTAL LINES AND KNOWN VARIETY

'KLEKB24053' is distinguished from its parents as described in Table 1:

TABLE 1

| Comparison with Parental Lines | | | |
|---|---|---|---|
| Charac-teristic | Variety 'KLEKB24053' | Female parent 'KA-2017-FV13018' | Male Parent '1106-4' |
| Branching | Good branching compared to the male and female parents | Poor branching compared to 'KLEKB24053' | Poor branching compared to 'KLEKB24053' |
| Vigor | Highly vigorous compared to the male and female parents | Less vigorous than 'KLEKB24053' | Less vigorous than 'KLEKB24053' |

'KLEKB24053' can be compared to the commercial variety 'Citrine von Dümmen Orange' (patent status unknown). Differences between the two varieties are described in Table 2:

TABLE 2

| Comparison with Similar Variety | | |
|---|---|---|
| Trait | 'KLEKB24053' | Commercial line 'Citrine von Dümmen Orange' |
| Flower color | Bicolor flower with a large orange center | Bicolor flower with a small and tiny orange center |

I claim:

1. A new and distinct variety of *Kalanchoe* plant named 'KLEKB24053' as shown and described herein.

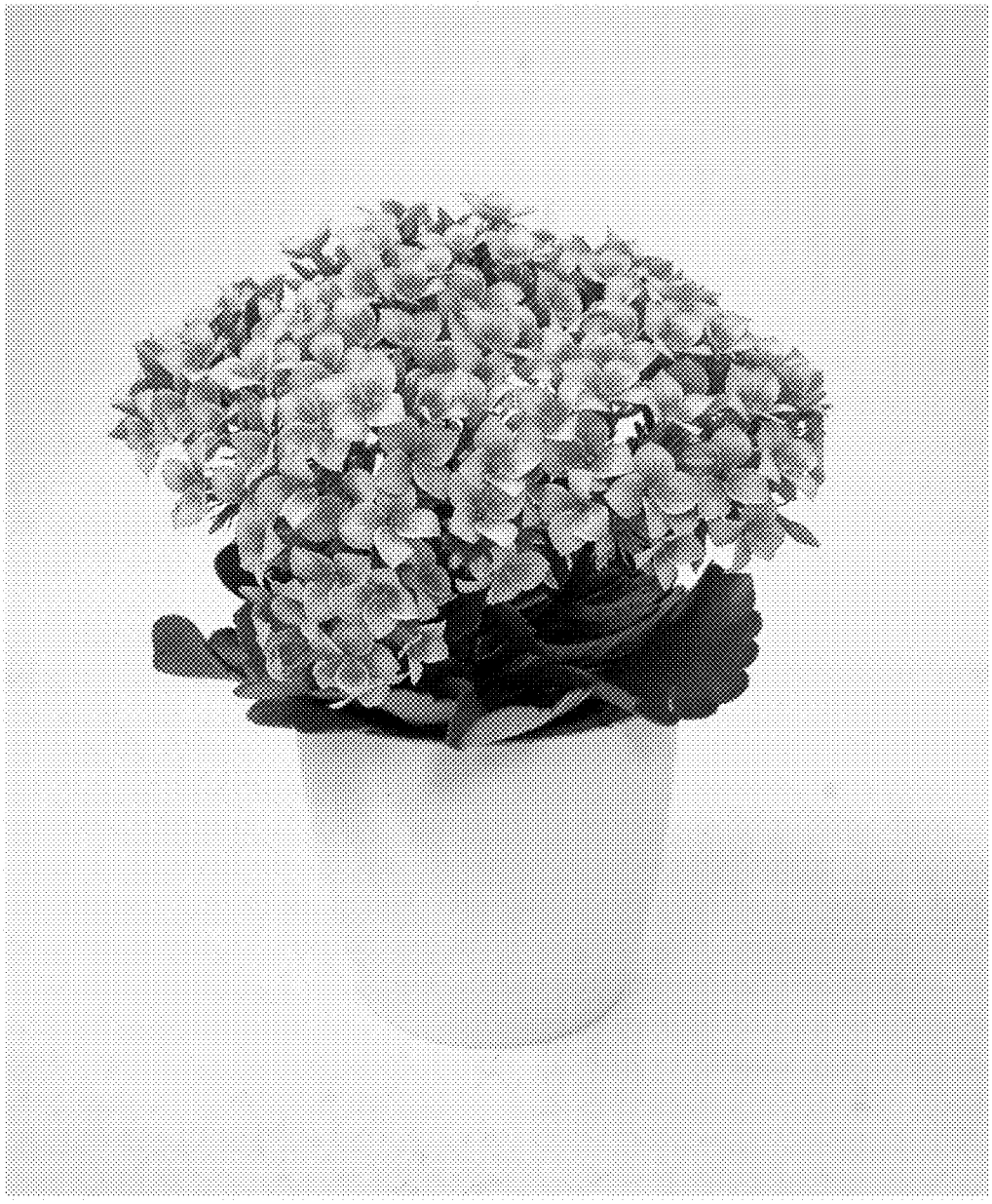

* * * * *